United States Patent
Shastri et al.

(10) Patent No.: US 7,005,269 B2
(45) Date of Patent: Feb. 28, 2006

(54) ERAAP MODULATORS REGULATE IMMUNE RESPONSES

(75) Inventors: Nilabh Shastri, Richmond, CA (US); Thomas Serwold, El Cerrito, CA (US)

(73) Assignee: The Regents of the University of California, Oakland, CA (US)

(*) Notice: Subject to any disclaimer, the term of this patent is extended or adjusted under 35 U.S.C. 154(b) by 327 days.

(21) Appl. No.: 10/164,012

(22) Filed: Jun. 6, 2002

(65) Prior Publication Data
US 2003/0228314 A1    Dec. 11, 2003

(51) Int. Cl.
*G01N 33/53*    (2006.01)
*C12Q 1/37*    (2006.01)
*C12N 9/48*    (2006.01)

(52) U.S. Cl. .............. 435/7.21; 435/24; 435/212; 435/326

(58) Field of Classification Search ............. 424/185.1; 530/330; 435/7.21, 24, 212, 326
See application file for complete search history.

(56) References Cited

OTHER PUBLICATIONS

Hattori et al, Biol Pharm Bull 27(6): 777-780, 2004.*
Stryer et al, in Biochemsitry, Third edition, W H Freeman Company, New York, pp. 31-33, 1998.*
Ngo et al, 1994, The Protein Folding Problem and Teritary Structure Prediction, pp. 492-495.*
Serwold et al, Nature Immunology 2(7): 644-651, Jul. 1999.*
Beninga et al, J Biol Chem 273(30): 18734-18742, 1998.*
Ocain et al, Biochem Biophys Res Commun 145(3): 1038-1042, Jun. 1987.*
Ocain et al, J Med Chem 31(11): 2193-2199, Nov. 1988.*
Weiss et al, Res Commun Chem Pathol Pharmacol 62(1): 113-123, Oct. 1988.*
Saveanu et al, Molecular Immunology 39: 203-215, 2002.*

* cited by examiner

*Primary Examiner*—Christina Chan
*Assistant Examiner*—Phuong Huynh
(74) *Attorney, Agent, or Firm*—Richard Aron Osman

(57) ABSTRACT

An immune response is modulated by selectively inhibiting ERAAP (an acronym for ER aminopeptidase associated with antigen processing) and confirming a resultant immune response modulation. More particularly, the method comprises contacting a patient determined to be in need of immune response modulation with a physiologically acceptable dosage composition comprising an effective amount of an inhibitor of ERAAP activity; confirming a resultant inhibition of said ERAAP activity and confirming a resultant immune response modulation in the patient. A variety of selective inhibitors are shown to be effective, including amino thiols, such as leucine thiol, ERAAP-specific antibody complementarity-determining region, and an ERAAP-specific siRNA.

8 Claims, No Drawings

ERAAP MODULATORS REGULATE IMMUNE RESPONSES

This invention was made with Government support under Grant No. AI39548 awarded by the National Institutes of Health. The Government has certain rights in this invention.

INTRODUCTION

1. Field of the Invention

The field of the invention is method for modulating immune responses by selectively inhibiting the aminopeptidase, ERAAP.

2. Background of the Invention

The identification of key molecules that regulate the immune system provide attractive targets for manipulation of the immune system in health and disease. The antigen processing pathways generate peptides as well as other material for presentation by the MHC molecules to the cells of the innate (e.g. NK cells) and adaptive (e.g. CD4 and CD8 T cells) immune system. The signals generated by the recognition of the appropriately loaded MHC molecules are essential for immune responses as well as tolerance to foreign pathogens, tumors and in autoimmunity. Prior to our invention, only one protease, the multicatalytic, cytosolic proteasome was known to be involved in the generation of peptides presented by MHC I molecules. Because the proteasome is also involved in numerous pathways essential for normal functioning of cells, inhibition of proteasome activity results in severe effects generally resulting in cell death. Accordingly it has been found that the absence of the proteasome in gene knock-out animals is lethal. Evidence for other proteolytic enzymes in the antigen processing pathway is only circumstantial at best. Thus, means to manipulate the normal display of peptides by the MHC I molecules were hitherto not available.

Our invention includes the identification and isolation of a proteolytic enzyme with ER aminopeptidase activity (termed ERAAP) that plays a key role in the major histocompatibility class I (MHC I) antigen processing pathway. Antigens presented by classical and non-classical MHC I molecules are vital in eliciting innate and adaptive immune responses to pathogens, tumors, and transplants as well as in autoimmunity. This aminopeptidase has been shown to reside in the endoplasmic reticulum (ER) and is involved in proteolytic trimming events that occur in the ER and are important for the generation of peptide/MHC I complexes.

Manipulation of the expression and/or activity of ERAAP influences the peptide presentation by the MHC I family of molecules. The ability to influence the peptide/MHC display permits manipulating immune responses to pathogens, tumors, self-tissues in autoimmunity as well as vaccines. As compared with the proteasome, manipulating the activity of ERAAP provides an alternative target which exists in a different intracellular compartment (ER versus the cytoplasm) and does not result in cell death. ERAAP therefore provides a far more attractive target for manipulating the antigen processing pathways for the family of MHC molecules.

In particular, we show that specific inhibitors of ERAAP downmodulate immune responses, with applications in autoimmunity, hypersensitivity, transplantation, etc. We find that we can manipulate immune responses by ectopic expression of ERAAP to other intracellular compartments or tissues, as well as by targeting ERAAP by other means such as antibodies. Appropriate mutations in ERAAP structure or active site allow it to target other antigen processing pathways as well, or function as an inhibitor of antigen processing.

Relevant Literature

We have described aminopeptidase activity in the endoplasmic reticulum (Serwold et al., Nature Immunol 2001 July, 2, 644–51). ERAAP has been previously identified as a leucine aminopeptidases involved in regulating blood pressure (e.g. Hattori et al., J Biochem (Tokyo). 2000 November;128(5):755–62; Hattori et al., J Biochem (Tokyo) 1999 May;125(5):931–8; Yamamoto et al., Hum Mutat. 2002 March;19(3):251–7). Additional relevant literature is cited herein.

SUMMARY OF THE INVENTION

The invention provides methods for modulating an immune response in an animal by selectively inhibiting ERAAP (ER aminopeptidase associated with antigen processing) and confirming a resultant immune response modulation in the animal. More particularly, the method comprises contacting a patient determined to be in need of immune response modulation with a physiologically acceptable dosage composition comprising an effective amount of an inhibitor of ERAAP activity; confirming a resultant inhibition of said ERAAP activity and confirming a resultant immune response modulation in the patient. A variety of selective inhibitors are shown to be effective, including amino thiols, such as leucine thiol, ERAAP-specific antibody complementarity-determining region (CDR), and an ERAAP-specific siRNA.

DETAILED DESCRIPTION OF PARTICULAR EMBODIMENTS OF THE INVENTION

A particularly recited method comprises contacting a patient determined to be in need of immune response modulation with a physiologically acceptable dosage composition comprising an effective amount of an inhibitor of ERAAP activity.

The recited patient is typically a human patient, but also includes animal, particularly mammalian patients such as dogs and cats encountered in veterinary applications, and rats and mice encountered in biomedical research applications. Hence, the need for immune response modulation will generally originate with the patient, but may also be that imposed by the biomedical researcher. In a particular embodiment, the patient is a human predetermined to be in medical need of immune suppression, more particularly, in need of suppression of antigen processing and/or presentation, such as a patient suffering from an immune hypersensitivity disorder, or a current or prospective graft recipient.

The targeted ERAAP is a well-known, naturally-occurring aminopeptidase, which has been biochemically characterized and cloned in a wide variety of animal species, including mice, rats and humans. Though we use human source ERAAP for our studies, such as to demonstrate inhibitor selectivity, similar biochemical specificity is found across the ERAAP from alternative species. Note that the same enzyme has been called "A-LAP" (adipocyte-derived leucine aminopeptidase) by others (e.g. Hattori et al., supra). Selective inhibitors are shown to preferentially inhibit ERAAP as compared with a panel of other aminopeptidases.

Protocols for delivering the inhibitor and effective dosages are known in the art and/or readily determined empirically by those skilled in the art guided by the selected inhibitor and the present disclosure. Structural requirements of ERAAP aminopeptidase inhibition have been clarified at both the enzyme and gene expression levels; hence, a wide variety of alternative inhibitors may be employed, guided by efficacy, physiological compatibility and convenience. For example, the well-characterized structural interaction between aminothiol inhibitors of aminopeptidases (e.g. Bienvenue et al., J Inorgan Biochem 2000, 78, 43–54) were exploited to select ERAAP selective aminothiol-type inhibitors. In this manner, we screened panels of compounds and identified a number of ERAAP-selective aminothiol inhibitors, including leucine thiol and lysinethiol. ERAAP modulation assays may be performed by any convenient protocol, including those described by us in Serwold et al. (2001, supra), those of Hattori et al. (2000, supra), etc. We further demonstrate that these ERAAP-selective inhibitors may be derivitized and conjugated to alternative ERAAP-selective inhibitors, such as isoleucinethiol. Alternative aminopeptidase inhibitor pharmacophores for ERAAP selectivity and method compatibility screens include L-bis (1-thio-2-amino-4-methylpentane) dihydrochloride (TAMP) and L-bis (1-thio-2-amino-3-phenylpropane) dihydrochloride (TAPP) (see, e.g. Weiss et al., Res Comm Chem Path Pharmacol 1988, 62, 113–2) and alpha-thiolbestatins (e.g. Ocain et al., J Med Chem 1988 November;31(11):2193–9).

We demonstrated a number of alternative modes of inhibiting ERAAP. For example, ERAAP-specific antibodies, intrabodies and fragments thereof comprising one or more ERAAP-specific complementarity-determining region (CDR) provide effective inhibition of ERAAP activity. We also were able to modulate ERAAP activity at the level of ERAAP transcripts using RNAi (see below). In particular, ERAAP-specific siRNAs were used to selectively inhibit ERAAP activity in a protocol adapted to both in vitro and in vivo use (e.g. Elbashir et al. Nature. 2001 May 24;411 (6836):494–8; Yu et al., Proc Natl Acad Sci USA 2002, 99,6047–52; Caplen et al. Hum Mol Genet 2002 January 15;11(2):175–84).

Inhibition is also effected at the genomic level by targeted disruption of ERAAP alleles in transgenic animals. We used a conventional disruption protocol: the mouse genomic ERAAP gene was isolated from a BAC library constructed from a mouse strain 129 embryonic stem (ES) cell line. The ERAAP targeting construct was linearized with NotI and transfected into CJ7 ES cells by electroporation. Clones were screened and positive pools identified by PCR and further confirmed by Southern blot analysis. Positive ES clones were injected into C57BL/6 blastocysts and surgically implanted into pseudopregnant females to generate chimeric mice. The chimeras are crossed with C57BL/6 females, resulting in mice with germline transmission. The ERAAP-/- mice were obtained by intercrossing.

Immuno-modulation as a result of ERAAP inhibition at the animal level may be detected in any convenient manner, and established protocols for measuring immunodeficiency are applicable, particularly protocols applied to other lesions in antigen presentation, such as MHC deficienies. For example, our ERAAP-/- mice present downregulated MHC and CD8 expression, reduced T8-lymphocyte numbers, and APC's not recognized by resident T8 cells, as assayed by flow cytometry of peripheral blood leukocytes and APC assays such as described below. The animals also present a number of phenotypic indicia of immunosupression, including reduced spleen and thymus volume. Functionally, the animals demonstrate reduced resistance to viral challenge (e.g. influenza and lymphocytic coriomeningitis virus) and a reduced graft-host response (e.g. skin graft assays).

Immune modulation was also assayed in animals as a function of pharmacological inhibition of ERAAP. For example, administration of panels of aminothiols to Sprague-Dawley rats, provided in food slurry at concentrations ranging from 10^-1 to 10^-4 mg/ml reveal a dosage dependent inhibition ERAAP and resultant immune response modulation. For APC assays, isolated peripheral blood leukocytes from treated and control animals are used as antigen presenting cells (APC) for a panel of T cells specific for different endogenous peptides presented by $K^b$ or $D^b$ MHC I molecules (below). hi these assays, exemplary leucinethiol-treated animals demonstrate a pronounced inhibition of APC function. These treated rats also present phenotypic indicia of immunosupression (supra), including reduced spleen and thymus volume. Functionally, the animals demonstrate reduced resistance to viral challenge (e.g. influenza and lymphocytic coriomeningitis virus) and a reduced graft-host response (e.g. skin graft assays).

The inhibitors are typically administered in the form of a pharmaceutical composition comprising at least one recited ERAAP inhibitor and a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition. Such carriers are well known in the pharmaceutical art as are procedures for preparing pharmaceutical compositions.

Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion. The dosage forms may include a variety of other ingredients, including binders, solvents, bulking agents, plasticizers etc. Preferred inhibitors are orally administrable to human patients, meaning they are both safe and effective when orally administered.

A wide variety of orally administrable compositions may be used. In a particular embodiment, the oral compositions are provided in solid discrete, self-contained dosage units, such as tablets, caplets, lozenges, capsules, gums, etc., which may comprise or be filled with liquid or solid dosage of the inhibitor. A wide variety of dosages may be used, depending on the application and empirical determination; typical dosages range from 10 ng to 1 mg. Injectable compositions are typically based upon injectable sterile saline or phosphate-buffered saline or other injectable carriers known in the art. As before, the inhibitor compound in such compositions is typically a minor component, often being from about 0.05 to 10% by weight with the remainder being the injectable carrier and the like. The above described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose. The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

Our protocol also recites confirming a resultant inhibition of said ERAAP activity and confirming a resultant immune response modulation in the patient. ERAAP inhibition may be confirmed directly according to any ERAAP assay disclosed herein, or indirectly by any convenient indirect, selective measure of ERAAP activity, such as the generation of an ERAAP inhibition-selective host response. Similarly, the resultant immune response modulation may be confirmed according to any metric disclosed herein, such as an antigen presentation function, or any other convenient direct or indirect selective measure of a resultant immune response change in the patient.

In another embodiment, the invention provides methods for modulating an immune response by contacting a cell determined to be targeted for immune response modulation with a physiologically acceptable dosage composition comprising an effective amount of an inhibitor of ERAAP (an acronym for ER aminopeptidase associated with antigen processing) (also known as A-LAP, an acronym for adipocyte-derived leucine aminopeptidase) activity; confirming a resultant inhibition of said ERAAP activity and confirming a resultant immune response modulation in the cell. As above, a variety of inhibitors may be employed, particularly inhibitors comprising, or consisting essentially of, a functional moiety selected from the group such as a non-hydrolyzable leucine moiety, an ERAAP-specific antibody complementarity-determining region (CDR), and an ERAAP-specific siRNA (an acronym for small interfering ribose nucleic acid). Depending on the nature of the target cell, the immune response modulation readout may be measured as change in antigen presentation or other cellular level immune response function. The target cell may be in vitro or in situ, as naturally present in the host animal.

Examplary Experimental Protocols

Immune surveillance by CD8 T cells depends upon the display of antigenic peptides by MHC class I molecules on the surface of potential target cells. The peptides are generated from endogenously synthesized proteins by cytoplasmic proteases and by another unknown protease in the endoplasmic reticulum (ER). Here we have identified the ER aminopeptidase associated with antigen processing or ERAAP. ERAAP resides in the ER, has a broad substrate specificity, and its expression is strongly upregulated by gamma interferon. Selective inhibition of ERAAP expression (e.g. by antagonists, RNA interference or immunotherapy) prevents trimming of peptides for MHC I molecules in the ER, and significantly reduces the expression of MHC I on the cell surface, and thereby provides a mode of modulating immune responsiveness.

MHC class I molecules display thousands of different peptides on the cell surface that are derived from the proteolysis of virtually all intracellular proteins (1). The presence of foreign proteins in infected or tumorigenic cells is advertised in the form of novel peptides presented by MHC I, which targets the cells for killing by cytotoxic CD8 T cells. This impressive diversity of peptides can be presented by MHC I molecules because they require the peptides they bind only to have one or two conserved residues, and a very well defined length.

The peptides available to MHC I molecules are initially generated in the cytoplasm by the proteasome and perhaps other proteases (2, 3). However, cytoplasmic proteolysis usually does not generate peptides with the precise length required by MHC I molecules, and instead generates extended intermediates (4, 5). Accumulating evidence suggests that the final trimming of these extended peptides occurs in the ER, where MHC I molecules are loaded. Our previous studies indicated that this trimming was mediated by an aminopeptidase (6–8).

To identify this protease, we biochemically purified the predominant aminopeptidase activity present in the ER. Microsomes from liver and spleens of mice were solubilized in detergent and the aminopeptidase activity was monitored by the colorimetric substrate leucine-p-nitroanilide (9). Ion exchange chromatography of solubilized microsomes revealed a predominant activity peak which was blocked by the aminopeptidase inhibitor leucinethiol. This activity was precipitated from solubilized microsomes by ammonium sulfate, resolublized and fractionated by size exclusion, ion exchange and hydrophobic interaction chromatographies. The highly enriched fractions from the final purification step contained a major band of approximately 100 kD on a coommassie blue stained SDS-PAGE gel. This band was subjected to in-gel trypsin digestion and the peptides were analyzed by MALDI-TOF mass spectrometry; the resulting tryptic peptide fingerprint was used to search the NCBI database (10). In two independent experiments 25 masses matched the predicted output of trypsin digested murine adipocyte-derived leucine aminopeptidase (Genbank Accession # AF227511). This assignment was further confirmed with the amino acid sequences of four peptides determined by high energy CID MS-MS analysis (11). This 930 amino acid murine aminopeptidase and its human and rat homologues are known by a variety of different names (12). Based upon the evidence presented here we refer to this enzyme as ERAAP, for ER aminopeptidase associated with antigen processing, to accurately designate its intracellular location and function in trimming peptides in the MHC I antigen processing pathway.

ERAAP is a member of the M1 family of zinc metalloproteases defined by the presence of a highly conserved motif within the core peptidase unit (13). The N-terminus contains a hydrophobic leader sequence suggesting that it may be cotranslationally translocated into the ER. Hydrophobicity plots did not predict any other transmembrane domains, and there were no other obvious motifs to predict its intracellular location. To determine whether ERAAP was secreted or retained intracellularly, COS cells were transfected with the murine ERAAP cDNA and western blots were performed with the whole cell lysates as well as the culture supernatants (14). A single band close to the predicted molecular weight of 106 kD was detected in the cell pellet but only faintly in the culture supernatant showing that the bulk of ERAAP was retained within the cell.

To establish the intracellular location of ERAAP, we performed pulse chase analysis using mouse EL4 cells (15). The cells were labeled briefly with $^{35}$S-methionine, chased for the indicated time periods, and immunoprecipitated with anti-ERAAP antiserum. The immunoprecipitates were treated with Endoglycosidase H (EndoH), which removes the high mannose oligosaccharides from ER proteins, but cannot cleave the modified oligosaccharides of proteins that have traversed through the golgi. The approximately 100 kD ERAAP band was detected at the beginning of the chase and was sensitive to EndoH as indicated by the decrease in its apparent molecular weight. Most importantly, ERAAP was sensitive to EndoH over the entire eight hour period of chase indicating that it was retained in an early secretory compartment.

To visualize directly the intracellular location of ERAAP, COS cells expressing murine ERAAP were stained with antiserum to ERAAP and analyzed by immunofluorescence microscopy (16). A reticular, perinuclear staining pattern characteristic of the ER was observed specifically in cells transfected with ERAAP, but not in vector transfected cells. Furthermore, ERAAP largely co-localized with the ER markers BiP and gp96. Based on the biochemical and immunofluorescence analysis we conclude that ERAAP is an ER resident protein.

MHC I molecules are expressed by virtually all tissues. To determine whether ERAAP expression correlated with that of MHC I, seven different mouse tissues were analyzed by western blot for expression of ERAAP, MHC I and the housekeeping proteins actin and gp96 as controls. ERAAP was detected in all tissues analyzed but its expression was highest in the liver, lung, spleen and thymus, the same tissues which also expressed the highest levels of MHC I molecules. Furthermore, the expression of ERAAP was increased approximately 10-fold by treatment of cultured fibroblasts with the inflammatory cytokine interferon gamma, which also upregulates many other key components in the antigen processing pathway (17).

To assess directly the importance of ERAAP in generating peptides for presentation by MHC I molecules, we knocked down the expression of ERAAP in cells with small interfering RNA oligonucleotide duplexes (siRNA)(18). $L^d$-L cells were transfected with siRNA specific for either mouse ERAAP, or as a negative control human ERAAP, which differs by 8 nucleotides in the targeted region. Transfection of cells with siRNA complementary to mouse ERAAP dramatically reduced the amount of ERAAP by approximately 90%, while the oligos targeting human ERAAP had no effect. Cell surface levels of the MHC I molecules $K^k$ and $L^d$ decreased by 23% and 44% respectively in the ERAAP knock-down cells. Because empty MHC I molecules are not stably expressed on the cell surface, this result implicates ERAAP in peptide supply.

The role of ERAAP in generating specific peptide/MHC complexes was further tested in antigen presentation assays. C57BL/6 mouse fibroblast cells were transfected with siRNA directed against mouse or human ERAAP and were treated with interferon gamma to induce upregulation of the antigen processing pathway and MHC I expression. Western blots showed that the transfected cells responded to γ interferon by upregulating MHC I, as well as Lmp7 and PA28α, two proteins known to be involved in antigen processing (19). Notably cells transfected with the mouse siRNA, but not the control siRNA, failed to upregulate ERAAP. The siRNA treated C57BL/6 tail fibroblast cells were used as antigen presenting cells (APC) for a panel of T cells specific for different endogenous peptides presented by $K^b$ or $D^b$ MHC I molecules (6). The expression of two peptides presented by $K^b$ and $D^b$, and recognized by bm 19.4Z and LpAZ T cells respectively, was strongly inhibited in the cells transfected with the mouse ERAAP siRNA, relative to cells treated with the transfection reagent or the human siRNA. The presentation of another yet unknown peptide presented by $K^b$ to the 27.5Z T cell was slightly diminished, while that of two other peptides presented by $D^b$ to 30NXZ and 1AZ T cells was reproducibly enhanced. These results correlate with our previous study in which treatment of cells with the aminopeptidase inhibitor leucinethiol caused a similar inhibition and enhancement of the same peptides (6). Our data demonstrate that ERAAP plays a role in the generation of a large fraction of antigenic peptides. In addition, in the absence of ERAAP, levels of some peptides increase, possibly because ERAAP normally destroys those peptides, or because of decreased competition for binding MHC I from ERAAP-dependent peptides.

To confirm that ERAAP trims peptides specifically in the ER, we generated TAP deficient fibroblast transfectants which cannot import peptides from the cytoplasm into the ER. We directly targeted precursors into the ER of these cells by an ER translocation sequence (ES) allowing analysis of peptide processing exclusively in the ER (6, 20). Cells expressed one of two different precursors of the SHL8 peptide: one that directly yielded SHL8 after signal peptidase cleavage (ES-SHL8), and one that further required the removal of seven N terminal flanking residues to yield SHL8 (ES-[X7]SHL8). Knockdown of ERAAP specifically inhibited generation of the SHL8 peptide from the N-terminally extended precursor, as measured by the response of the SHL8/$K^b$-specific B3Z T cell. In contrast, knockdown of ERAAP had no effect on generation of SHL8 from the precursor that required no trimming. Therefore, ERAAP is specifically required for trimming extended precursors in the ER.

To determine its substrate specificity, purified ERAAP was incubated with the SHL8 peptide extended by various N-terminal amino acids (21). After 0, 30 or 90 minute incubations with the decapeptide substrates, the peptide digests were separated by HPLC and the products were detected using the B3Z T cell after conversion of all peptides to SHL8 with trypsin, as previously described (5). ERAAP cleaved the N-terminal lysine, leucine, tyrosine and asparagine residues to yield the nonamer and the octamer products in 30 minutes. In 90 minutes the SHL8 octapeptide was the predominant product, although smaller products could not be detected in this T cell based assay (22). In contrast, ERAAP completely failed to cleave the N-terminal lysine residue when it was followed by a proline residue. The inability to cleave the "X-Pro" bond had previously been established as a key characteristic of the ER aminopeptidase (6), and therefore indicates ERAAP is the aminopeptidase responsible for providing peptides for the many MHC I molecules that present peptides with the "X-Pro-Xn" motif The otherwise broad specificity of ERAAP suits its role in cleaving a wide spectrum of peptides for MHC I molecules.

The identification of ERAAP answers an enduring question in the MHC class I antigen processing pathway—how cells produce thousands of distinct peptides cleaved to the precise lengths required for binding MHC I molecules in the ER (4, 23). Recent studies have indicated that proteolysis of antigenic precursors in the cytoplasm rarely yields the final peptide (3, 24). The discovery of ERAAP and its role in trimming peptides in the ER provides the key missing link between the products of cytoplasmic processing and the final peptides presented by MHC I on the cell surface. Manipulation of ERAAP function provides a useful therapeutic method to modulate immune response, particularly CD8 T cell-mediated responses.

REFERENCES AND NOTES

1. N. Shastri, S. Schwab, T. Serwold, *Annu Rev Immunol* 20, 463 (2002); E. G. Pamer, P. Cresswell, *Annu Rev Immunol* 15, 323 (1998).
2. K. L. Rock et al., *Cell* 78, 761 (1994); K. L. Rock, A. L. Goldberg, *Annu. Rev. Immunol.* 17, 739 (1999); E. Geier et al., *Science* 283, 978 (1999).
3. P.-M. Kloetzel, *Nature Reviews Molecular Cell Biology* 2, 179 (2001).
4. K. Falk, O. Rotzschke, H. G. Rammensee, *Nature* 348, 248 (1990).
5. P. Paz, N. Brouwenstijn, R. Perry, N. Shastri, *Immunity* 11, 241 (1999).
6. T. Serwold, S. Gaw, N. Shastri, *Nature Immunology* 2, 644 (2001).
7. N. Brouwenstijn, T. Serwold, N. Shastri, *Immunity* 15, 95 (2001).
8. D. Fruci, G. Niedermann, R. H. Butler, P. M. van Endert, *Immunity* 15, 467 (2001).
9. ERAAP was purified from microsomes of mice, prepared as described in (7).
10. U. Hellman, C. Wernstedt, J. Gonez, C. H. Heldin, *Anal Biochem* 224, 451 (1995); K. R. Clauser, P. Baker, A. L. Burlingame, *Anal Chem* 71, 2871 (1999); I. Helen, E. D. Field, *Proteomics* 2, 36 (2001).
11. K. F. Medzihradszky et al., *Anal Chem* 72, 552 (2000).
12. A. Hattori, H. Matsumoto, S. Mizutani, M. Tsujimoto, *J. Biochem* (Tokyo) 125, 931 (1999); L. Schomburg, H. Kollmus, S. Friedrichsen, K. Bauer, *Eur. J. Biochem.* 267, 3198 (2000); H. Miyashita et al., *Blood* 99, 3241 (2002).
13. N. D. Rawlings, E. A. O'Brien, A. J. Barrett, *Nucleic Acids Res* 30, 343 (2002).
14. COS cells were transfected using Fugene 6 (Roche) according to manufacturers instruction with either pcDNA1 (Invitrogen), or pcDNA1/murine ERAAP cloned by RT-PCR. After 48 hours, cells were harvested. Equal fractions of cells ($2\times10^3$) and supernatant (10 $\mu$L) were separated by SDS PAGE, and blotted onto 0.45 $\mu$m nitrocellulose (Amersham). Western blots were performed with 2 $\mu$g/ml affinity purified rabbit antiserum generated against an N-terminal ERAAP peptide, and a donkey anti rabbit peroxidase-conjugated secondary antibody (Amersham).
15. EL4 cells ($3.5\times10^{7}$) were starved for methionine for 10 minutes, then labelled for 15 minutes with 100 $\mu$Ci/ml EasyTag 35-S labeling mix (Dupont NEN) in medium +2% dialized FCS. Cells were put into fresh medium containing 10 mM unlabelled methionine. At the indicated time points, $8\times10^6$ cells were removed. Cells were lysed for 30 min on ice in 1 ml PBS, 1% Triton X-100 containing protease inhibitors. The solubilized material was precleared with Staph A and Staph G (Zymed Laboratories) plus rabbit serum. Then protein A+G beads (Zymed) pre-incubated with Rabbit anti-ERAAP were added and rocked for 2 hours. Immunoprecipitated material was washed extensively, and was then resuspended in SDS sample buffer and divided into two equal parts. One part was treated for 1 hour at 37° C. with 500 units EndoH (New England Biolabs) and the other left untreated. Samples were separated by SDS PAGE and analyzed by autoradiography.
16. COS cells were transfected as described in (14) and analyzed by immunofluorescence staining (26).
17. U. Boehm, T. Klamp, M. Groot, J. C. Howard, in *Annu Rev Immunol* 15, 749 (1997).
18. The coding strands of the RNA oligonucleotide duplexes were directed to the 5' end of mouse or human ERAAP mRNA (Dharmacon). The oligo targeting lamin b1 was has been described (25). All oligonucleotides had 3' dTdT overhangs. RNA duplexes were annealed as recommended by the manufacturer. L cells expressing $L^d$ ($L^d$-L) or tail fibroblast cell lines from C57BL6 (B6) wild type or B6.tm$^{TAP-/-}$ knockout mice were grown in 24-well dishes and oligonucleotides were transfected into cells using oligofectamine (Invitrogen) according to manufactures instructions. Seventy two hours after transfection, cells were assayed by western blot, flow cytometry, and/or antigen presentation. For flow cytometry, monocloonal antibodies 30-5-7S (anti-$L^d$), Y3 ($K^k$) were used, and secondary fluorescein conjugated goat anti-mouse IgG. Flow cytometry was performed on a FacScan (Coulter). For antigen presentation assays, cells were titrated in 96-well plates, and the indicated LacZ inducible T cell hybridomas were added at $10^5$/well. T cell activation was monitored by the accumulation of LacZ using chlorophenolred-$\beta$-D-galactopyrannoside as a substrate, as described previously (6).
19. H. J. Fehling et al., *Science* 265, 1234 (1994); T. Preckel et al., *Science* 286, 2162 (1999).
20. K. Anderson et al., *J. Exp. Med.* 174, 489 (1991).
21. ERAAP purified from mouse microsomes through the ion-exchange step as described in (9). Each reaction contained 50 uL ERAAP (equivalent to 0.12 nmoles LPNA cleaving activity/gL/min) and 3 pmoles peptide substrate in PBS +0.1% triton X-100. The reactions were stopped at the indicated times by adding 400 $\mu$L 10% acetic acid. Peptide mixture was separated by reverse phase HPLC and assayed as described earlier to allow detection of N-terminally extended analogs (5).
22. N. Shastri, F. Gonzalez, *J. Immunol.* 150, 2724 (1993).
23. K. Falk, O. Rotzschke, S. Stevanovic, G. Jung, H.-G. Rammensee, *Nature* 351, 290 (1991).
24. P. Cascio, C. Hilton, A. F. Kisselev, K. L. Rock, A. L. Goldberg, *Embo Journal* V20, 2357 (2001); R. E. M. Toes et al., *J. Exp. Med.* 194, 1 (2001).
25. S. M. Elbashir et al., *Nature* 411, 494 (2001).
26. J. G. Egen, J. P. Allison, *Immunity* 16, 23(2002)

The foregoing descriptions of particular embodiments and examples are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification and all references cited therein are herein incorporated by reference as if each individual publication or patent application or reference were specifically and individually indicated to be incorporated by reference. Any material accompanying this application on compact disc or other recorded medium is incorporated by reference.

What is claimed is:

1. A method of inhibiting MHC class I antigen processing by ERAAP, wherein ERAAP is an acronym for ER aminopeptidase associated with antigen processing, the method comprising the steps of:

administering to a host cell in vitro, expressing said ERAAP, and predetermined to be in need of suppression of antigen processing or antigen presentation an effective amount of an ERAAP inhibitor, and wherein the inhibitor is selected from the group consisting of leucine-thiol, lysine-thiol and isoleucine-thiol; and confirming a resultant inhibition of said ERAAP and inhibition of said MHC class I antigen processing.

2. The method of claim 1, wherein the inhibitor is leucine-thiol.

3. The method of claim 1, wherein the inhibitor is lysine-thiol.

4. The method of claim 1, wherein the inhibitor is isoleucine-thiol.

5. A method of inhibiting MHC class I antigen processing by ERAAP, wherein ERAAP is an acronym for ER aminopeptidase associated with antigen processing, the method comprising the steps of:

administering to a host cell in vitro, expressing said ERAAP and predetermined to be in need of suppression of antigen processing or antigen presentation an effective amount of an ERAAP inhibitor, and wherein the inhibitor is a pharmacophore selected from the group consisting of L-bis(1-thio-2-amino-4-methylpentane) dihydrochloride (TAMP), L-bis(1-thio-2-amino-3-phenylpropane)dihydrochloride (TAPP) and an alpha-thiolbestatin; and confirming a resultant inhibition of said ERAAP and inhibition of the MHC class I antigen processing.

6. The method of claim 5, wherein the pharmacophore is L-bis(1-thio-2-amino-4-methylpentane)dihydrochloride (TAMP).

7. The method of claim 5, wherein the pharmacophore is L-bis(1-thio-2-amino-3-phenylpropane)dihydrochloride (TAPP).

8. The method of claim 5, wherein the pharmacophore is an alpha-thiolbestatin.

* * * * *